US00RE40023E

(19) United States
(12) Reissued Patent
DeSimone

(10) Patent Number: US RE40,023 E
(45) Date of Reissued Patent: Jan. 22, 2008

(54) DIETARY AND PHARMACEUTICAL COMPOSITIONS CONTAINING LYOPHILIZED LACTIC BACTERIA, THEIR PREPARATION AND USE

(76) Inventor: Claudio DeSimone, Via Fabretti, 8, 00161 Roma (IT)

(21) Appl. No.: 11/375,704

(22) Filed: Mar. 15, 2006

Related U.S. Patent Documents

Reissue of:
(64) Patent No.: 5,716,615
Issued: Feb. 10, 1998
Appl. No.: 08/448,787
Filed: May 24, 1995

U.S. Applications:

(63) Continuation of application No. 08/117,751, filed on Sep. 8, 1993, now abandoned, which is a continuation-in-part of application No. 07/983,839, filed on Dec. 1, 1992, now abandoned.

(30) Foreign Application Priority Data

Feb. 10, 1992 (IT) ..... MI92A0256

(51) Int. Cl.
*A61K 38/44* (2006.01)
*C12N 1/04* (2006.01)
*C12N 1/20* (2006.01)

(52) U.S. Cl. ..... 424/93.4; 424/93.44; 424/93.45; 426/61; 435/252.4; 435/252.9; 435/253.4; 435/260; 435/856; 435/885

(58) Field of Classification Search ..... None
See application file for complete search history.

(56) References Cited

U.S. PATENT DOCUMENTS

| | | | | | |
|---|---|---|---|---|---|
| 4,115,199 | A | * | 9/1978 | Porubcan et al. | 435/252.4 |
| 4,205,132 | A | * | 5/1980 | Sandine et al. | 435/260 |
| 4,226,940 | A | * | 10/1980 | Storrs | 435/260 |
| 4,588,595 | A | * | 5/1986 | Okonogi et al. | 435/252.4 |
| 4,806,368 | A | * | 2/1989 | Reddy | 426/61 |
| 4,913,913 | A | * | 4/1990 | Takano et al. | 426/43 |
| 5,108,766 | A | * | 4/1992 | Gelinas et al. | 426/43 |
| 5,128,260 | A | * | 7/1992 | Mathison | 435/252.1 |
| 5,143,845 | A | * | 9/1992 | Masuda | 435/252.4 |
| 5,219,597 | A | * | 6/1993 | Mok et al. | 426/28 |
| 5,474,932 | A | * | 12/1995 | Bengmark et al. | 435/252.9 |

FOREIGN PATENT DOCUMENTS

| | | | |
|---|---|---|---|
| EP | 0 228 881 | * | 7/1987 |
| EP | 0 291 578 | * | 11/1988 |
| FR | 2609044 | * | 3/1987 |
| IT | 1200625 | * | 1/1989 |

OTHER PUBLICATIONS

Fernandes et al, FEMS Microbiology Reviews, "Therapeutic Role Dietary Lactobacilli and Lactobacillic Fermented Dairy Products" 46, (1987), pp. 343–356.*
H. Goris et al, Microecology and Therapy, "Intestinal Flora Associated Endotoxin", 14, (1984), p. 267 (Abstract Only).*
D. Triger, Journal of Hepatology, "Endotoxemia in Liver Disease—Time for Re–Appraisal?" 12, (1991), pp. 136–138.*
A. Onderdonk et al, Obstetrics and Gynecology, "Quantitative and Qualitative Effects of Douche Preparation on Vaginal Microflora", 80, (1992), pp. 333–338.*
H. Kitazawa et al, Microbiol. Immunol., "Interferon Induction in Murine Peritoneal Macrophage by Stimulation with Lactobacillus acidophilus", 36, (1992), pp. 311–315.*
G. Kaklij et al, L Cancer Letters, "Antitumor Activity of Streptococcus thermophilus against Fibrosacoma: Role of T–cells", 56, (1991), pp. 37–43.*
H. Sawada et al, Agric. Biol. Chem., "Purification and Characterization of an Antihypertensive Compound from Lactobacillus casei", 54, pp. 3211–3219.*
G. Molin et al, Antonie Van Leeuwenhoek, "Effect of Fermented Oatmeal Soup on the Cholesterol Level and the Lactobacillus Collonization of Rat Intestinal Mucosa", 61, (1992), pp. 167–173.*
S. Klebanoff et al, J. Exp. Med. "Viricidal Effect of Lactobacillus acidophilus on Human Immunodeficiency Virus Type 1: Possible Role in Heterosexual Transmission", 174, (1991), pp. 289–292.*
S. Klebanoff et al, The Journal of Infectious Diseases, "Control of the Microbial Flora of the Vagina by Hydrogen Peroxide—Genrating Lactobacilli", 184, (1991), pp. 94–100.*
M. Hall et al, Archives of Disease in Childhood, "Factors Influencing the Presence of Faecal bactobacilli in Early Infancy" 65, (1990), pp. 185–188.*
G.W. Elmer et al, JAMA, Vo. 275, pp. 870–876 (1996).*
Bifidobacteria Microflora, vol. 3, No. 1, pp. 29–33, 1984, T.*
Kageyama, et al, The Effect of Bifidobacterium Administration in Patients with Leukemia.*
N. Suegara, et al, "Hypolipidermic Effect of Streptococcus faecalis Kawai in Humans and Mechanisms of Serum Lipid Reduction", Microecology and therapy, vol. 15, pp. 271–280, 1985.*
Microecology and Therapy, vol. 16, pp. 271–271, 1986, D. Muting, et al, "Bifidobacterium Bifidus Adminsitration in Humans: A Controlled Clinical Study in Liver cirrhosis".*
Bifidobacteria microflora, vol. 1, No. 1, pp. 3–24, 1982, F. Mitsuoka, "Recent Trends in Research on Intestinal Flora".*
Microecology and Therapy, vol. 14, pp. 109–126, 1984, Y. Kawai, "Effect of Cellular Extracts of Streptococci on Hyper–lipidemia in Rats, Rabbits, and Humans".*
Patent Abstracts of Japan, vol. 9, No. 309 (C–318), Dec. 5, 1985, JP–A–60 149 527, Aug. 7, 1985.*
Database WPI, Derwent Publications, AN–89–119459, Sep. 4, 1987, JP–A–1 066 124, Mar. 13, 1989.*

* cited by examiner

*Primary Examiner*—Sandy Saucier
*Assistant Examiner*—Deborah K. Ware
(74) *Attorney, Agent, or Firm*—Morgan Lewis & Bockius LLP

(57) ABSTRACT

A pharmaceutical composition containing several different bacteria including Streptococcus thermophilus, Lactobacilli and Bifidobacteria is disclosed. The bacteria are present in the composition at a total concentration of $1\times10^{11}$ to $1\times10^{13}$ per gram. Further, methods of using the pharmaceutical are disclosed which include treatment of a gastrointestinal disorder and hypercholestermia. Also a method for modulating a host's immune response is disclosed.

33 Claims, No Drawings

DIETARY AND PHARMACEUTICAL COMPOSITIONS CONTAINING LYOPHILIZED LACTIC BACTERIA, THEIR PREPARATION AND USE

Matter enclosed in heavy brackets [ ] appears in the original patent but forms no part of this reissue specification; matter printed in italics indicates the additions made by reissue.

This application *is a reissue of application Ser. No. 08/448,787, filed May 24, 1995, now U.S. Pat. No. 5,716, 615, which* is a continuation of application Ser. No. 08/117, 751, filed on Sep. 8, 1993, now abandoned, which is a continuation-in-part of application Ser. No. 07/983,839, filed Dec. 1, 1992, now abandoned.

FIELD OF THE INVENTION

The present invention relates to dietary and pharmaceutical compositions useful for dietary or certain pharmaceutical indications, said composition containing lyophilized, lactic bacteria. Said compositions, being useful for prophylaxis or treatment of gastrointestinal disorders, or for treatment of hypocholesterolemia.

BACKGROUND OF THE INVENTION

In Bifidobacteria Microflora, Vol. 3(1), 29–33, 1984, the beneficial effect of administering Bifidobacterium to patients suffering from leukemia is described. In FEMS Microbiology Reviews 46 (1987), 343–356, the therapeutical function of lactobacilli is disclosed, while Nobuo Suegara et al., Microecology and Therapy, Vol. 15, 271–280 (1985) state that oral administration of S. faecalis KAWAI greatly improves the lipid metabolism in human beings and animals. From Microecology and Therapy, Vol. 14, 109–126 (1984) the effect of streptococcus cell extracts on hyperlipemia in rats, rabbits and human beings is known. Other references describing the beneficial action of lactobacilli or other strains of activated lactobacilli are for example Bifidobacteria Microflora 1, 3–24, 1982 Recent Trends in Research on Intestinal Flora, Microecology and Therapy 14, 267, 1984 (Intestinal Flora Associated Endotoxin), Microecology Therapy 16, 271–272, 1986 (Bifidobacterium bifidum administration in Humans: a Controlled Clinical Study in Liver Cirrhosis), etc.

In Italian Patent No. 1,022,625 food and pharmaceutical compositions which stimulates the production of gamma-interferon and contain lactobacilli Streptococcus thermophilus and Lactobacillus bulgaricus are described.

In U.S. Pat. No. 4,806,368, Reddy envisaged the possibility of preparing dietary fiber based tablets with Lactobacillus acidophilus and/or Bifidobacterium bifidus, Leuconostoc citrovorum and Propionibacterium shermanii. To enhance the viability of L. acidophilus in the tablets, a combination of aminoacids, vitamins, calcium, magnesium salts, lactose and dietary fiber were included. The optimal concentration of lactobacilli in each 750 mg tablet was not higher than $1\times10^7$. High concentrations were avoided.

Fernandes et al. in their comprehensive review "Therapeutic role of dietary lactobacilli and lactobacillic fermented diary products," published in FEMS Microbiology Reviews 46:343–356, 1987, indicate moreover the beneficial effects of lactobacilli, especially of L. acidophilus.

Takano et al., U.S. Pat. No. 4,913,913, describes a method for preparing a bifidobacteria-containing fermented milk, in which Lactobacilius casei and Bifidobacterium longum are cultivated in admixture or are mixed after being separately cultivated, and thus a bifidobacteria-containing lactic acid bacteria-fermented milk with an elevated survival rate of Bifidobacterium longum is obtained.

No suggestion is found in the literature to prepare a composition which combines several different lactic bacteria. In addition, there is no indication in the prior art to suggest administering to humans a concentration of lactobacilli exceeding $10^9$ per gram.

SUMMARY OF THE INVENTION

It has now been found that a composition comprising at least two lactic acid bacteria strains allows improved therapeutical results to be achieved of a kind never previously attained by prior art compositions, provided that the concentration of each of two lactic bacteria strains exceeds $10^{11}$ viable lactic bacteria/gram of composition.

It is therefore an object of the present invention to provide an appropriate dietary and pharmaceutical composition comprising lyophilized lactic bacteria at high concentration per gram of product ($>10^{11}$ bacteria/gram), qualitatively and quantitatively coordinated so as to be used for treatment or for prevention of certain gastrointestinal disorders, or for treatment or prevention of hypocholesterolemia or to potentiate the host's immune system. The composition of the present invention can be used in combination with any of a variety of compatible drugs.

The present composition can be used to antagonize the onset of diarrhea, constipation, hypercholesteremia, endotoxin absorption or production of endogenous toxic substances.

DESCRIPTION OF THE PREFERRED EMBODIMENTS

The compositions of the present invention comprise as essential active ingredients: (a) from 10 to 95% by weight of total composition of lyophilized lactic bacterium Streptococcus thermophilus, and (b) from 90 to 5% by weight of total composition of at least one further lyophilized lactic bacterium selected from the group consisting of Lactobacillus plantarum and Lactobacillus casei. An excipient in an amount of from 1 to 10% by weight of total components can be added, said amounts being all based on the total weight of the composition. The composition can be used in combination with a compatible pharmaceutical in an amount of from 1 to 20% by weight based on the total weight of the composition. It is essential that the viable bacteria concentration be at least $1\times10^{11}$ for (a) and $1\times10^{11}$ for (b) per gram of the composition. Preferably, the viable bacteria concentration of both (a) and (b) should be used between $1\times10^{11}$ and $1\times10^{13}$ per gram of the composition.

The compositions of the invention can be prepared with methods well-known to those skilled in dairy technology, enabling the presence of viable bacteria at concentrations ranging between $1\times10^{11}$ and $1\times10^{13}$ bacteria per gram of the composition.

According to a preferred embodiment, the composition should also contain from 85 to 5% by weight of one or more lyophilized lactic bacteria selected from bifidobacteria (preferably a mixture of lyophilized Bifidobacterium longum, Bifidobacterium bifidum, Bifidobacterium infantis, ratio of 1:1:1 by weight) at a concentration ranging between $1\times10^9$ and $1\times10^{12}$ viable bacteria per gram of the composition, lyophilized Lactobacillus acidophilus at a concentration of from $1\times10^9$ to $1\times10^{12}$ viable bacteria per gram of the composition, lyophilized lactobacillus delbruekii subspecies bulgaricus at a concentration of from $1\times10^9$ to $1\times10^{12}$ viable bacteria per gram of the composition, and lyophilized Streptococcus faecium at a concentration of from $1\times10^9$ to $1\times10^{12}$ bacteria per gram of the composition, optionally with 1 to 10% of an excipient and 1 to 20% of a compatible pharmaceutical.

A particularly preferred composition according to the present invention contains: a) 31% by weight of lyophilized Streptococcus thermophilus, $7\times10^{11}$; b) 7% by weight of lyophilized Lactobacillus casei, $1\times10^{11}$; c) 8% by weight of lyophilized Lactobacillus plantarum, $1\times10^{11}$; d) 7% by weight of lyophilized Lactobacillus acidophilus, $2\times10^{10}$; e) 8% by weight of lyophilized Lactobacillus delbrueckii subspecies bulgaricus, $3\times10^9$; f) 27% by weight of lyophilized bifidobacteria, $38\times10^{10}$; and g) 12% by weight of an excipient, wherein all the amounts are based on the total weight of the composition and Bifidobacterium Bifidum, Bifidobacterium longum and Bifidobacterium infantis.

As mentioned above, as further optional components the compositions of the invention may contain usual excipients as are conventionally used for preparing pharmaceutical compositions in which normally the ratio of the active ingredient to the excipient will range between 1:10 and 99:90.

The compositions of the invention can be made in conventional pharmaceutical forms, such as for example tablets, coated tablets, capsules, packets, solutions, sachets, suspensions, emulsions, suppositories, pellets, syrups, vaginal suppositories, and are prepared in the usual m manner by mixing active ingredients in the mentioned amounts, eventually adding excipients and/or carriers, adjuvants and/or dispersing agents. Water may be used as the diluent. Organic solvents can be used in the form of adjuvants. Adjuvants can be for example, non-toxic organic solvents such as paraffines, vegetable oils (peanut oil or sesame oil), glycerine, glycols (propylene glycol, polyethylene glycol), solid carriers such as for example natural mineral flours (kaolin, talc), synthetic mineral flours (silicates for example), sugar (cane sugar for example), emulsifiers (alkylsulfonates or arylsulfonates and the like), dispersants (lignin, methylcellulose, starch and polyvinylpyrrolidone, for example) and lubricants (magnesium stearate, talc, stearic acid, sodium laurylsolfonate, for example). Preferred excipients for the composition of the invention are maltodextrin, microcrystalline cellulose, maize starch, levulose, lactose and dextrose.

The administration takes place in the usual manner, preferably by oral route. In this case pharmaceutical forms adapted to this end can obtain, in addition to usual excipients, also additives such as sodium citrate, calcium carbonate, calcium dihydrogen phosphate, together with several additional substances such as starch, gelatin and the like. In case of liquid compositions compatible colouring agents of flavoring substances may be added.

As an optional component, the compositions may contain such compatible pharmaceuticals as anticholinergies, antihistamines, analgesics, adrenergics, antiinflammatories, antiseptics, hepatoprotective agents, or antilipemic drugs, in amounts of from 1 to 20% by weight, based on the total weight of the composition. As mentioned above, for preparing the compositions, the individual microorganisms in the dehydrated form are mixed in appropriate proportions and the mixture is then admixed with the excipients or optionally with other pharmaceuticals.

PHARMACOLOGICAL STUDIES

The following studies were carried out using a composition of lyophilized viable Streptococcus thermophilus and Lactobacillus plantarum, at concentrations respectively of $6\times10^{11}$ and $4\times10^{11}$ per gram of the composition.

The formulation of the preparation was in form of sachets, each containing 3 g of the composition. All the following studies were carried out in human health volunteers and in patients enrolled after informed consent according to the Helsinki declaration. Medical and laboratory controls were done by physicians aware of the good usual clinical practice (GPC) as stated by the European Economic Community (EEC). Statistical analysis was carried out by a statistician, not directly involved in the study. T0, T1, T2, and T3 refer respectively to pre-treatment, after one, two and three weeks of treatment.

EXAMPLE 1

In 33 patients affected by chronic hepatitis following C virus infection (anti-HCV+) the administration of one sachet per day (3 g of the composition containing 60% by weight of Streptococcus thermophilus and 40% by weight of Lactobacillus plantarum) induced a reduction of the aspartate aminostransferase (AST) from 52±32 IU at TO to 45±27 IOU at T2, of the alanine aminotransferase (ALT) from 68±39 IU at TO to 58±31 IU at T2 and of gamma-glutamyltranspeptidase (gGT) from 52±49 IU at TO to 40±25 IU at T2. In the above patients the following symptoms improved during and/or the treatment: anorexia, itching, nausea, diarrhea, constipation and insomnia. No undesired reactions or side-effects were noted. In 21 of the above patients, AST, ALT, and/or gGT resulted normalized at T3. As control group, 26 patients were treated with 15 capsules per day of Infloran Berna (trade mark), a marketed preparation of Bifidobacerium bifidum ($1\times10^9$ bacterial per capsule) and Lactobacillus acidophilus ($1\times10^9$ bacteria per capsule). The usual recommended daily dose of Infloran is 3 capsules per day; therefore the experiments were carried out administering a five fold increased dosage of Infloran. Apart from the poor compliance on the treated patients, no subject evidenced any significant variation in the AST, ALT and gGT levels at T3 (AST from 54±30 in AT to TO 55±31 IU; ALT from 65±34 IU at TO to 64±31 IU at T2 and gGT from 51±37 IU at TO to 55±41 IU at T2. The difference among the two groups was always statistically significant with p values <0.05.

EXAMPLE 2

In 24 subjects with serum cholesterol levels at TO of 268±126 mg/dl two sachets (6 gr per day of the composition comprising 68% by weight of Streptococcus thermophilus, 28% by weight of Lactobacillus casei and 4% by weight of maltodextrin) were administered, and at T3 the levels were reduced to 219±175 mg/dl (p<0.5). In the control group treated with 15 capsules of Infloran per day, the serum cholesterol levels did not change (from 254±156 mg/dl at TO to 250±168 mg/dl at T3)__.

EXAMPLE 3

Fifteen patients with irritable bowel syndrome were treated for 2 weeks with a sachet (3 g of the composition of Example 1) per day. Before and after the treatment colonscopy was performed and multiple endoscopic biopsies, at least 2 samples in each site, were taken in the descending and sigmoid colon. On biopsy specimens histological studies have shown a reduced number of infiltrating inflammatory cells. In the faeces of the same patients the measurement of tumor necrosis factor alpha has shown that the levels of this cytokine are reduced following the treatment with the preparation, from 45±12 pg/ml to faecal supernatant to 12±5 pg/ml ($p<0.01$).

EXAMPLE 4

In 18 healthy volunteers, the following parameters were evaluated before, during and at the end of the administration of one sachet (3 g) per day. In this study, the composition per gram was:

31% by weight of lyophilized Streptococcus thermophilus, $7\times10^{11}$

7% by weight of lyophilized Lactobacillus casei, $1\times10^{11}$

8% by weight of lyophilized Lactobacillus plantarum, $1\times10^{11}$

7% by weight of lyophilized Lactobacillus acidophilus, $2\times10^{10}$

8% by weight of lyophilized Lactobacillus delbrueckii sub-species bulgaricus, $3\times10^{9}$, 27% by weight of a mixture of lyophilized Bifidobacteria, $38\times10^{10}$, 12% by weight of microcrystalline cellulose.

| | T0 | T1 | T2 | T3 |
|---|---|---|---|---|
| | | CHOLESTEROL (mg/dl) | | |
| average | 190.6 | 179.0 | 174.4 | 184.2 |
| Maximum | 285.3 | 264.8 | 247.5 | 267.4 |
| Minimum | 108.3 | 118.1 | 108.6 | 113.6 |
| SD | 59.9 | 44.7 | 44.0 | 54.3 |
| | | AST (IU/ml) | | |
| average | 29.8 | 25.8 | 26.0 | 23.3 |
| Maximum | 97.3 | 88.1 | 81.5 | 59.1 |
| Minimum | 13.2 | 6.8 | 10.8 | 10.8 |
| SD | 23.1 | 22.0 | 19.1 | 13.7 |
| | | ALT (IU/ml) | | |
| average | 31.9 | 31.2 | 26.6 | 24.5 |
| Maximum | 131.6 | 132.6 | 99.1 | 91.0 |
| Minimum | 10.1 | 7.1 | 7.5 | 6.7 |
| SD | 34.5 | 35.4 | 26.3 | 24.1 |
| | | gG T (IU/ml) | | |
| average | 41.2 | 40.3 | 37.5 | 38.5 |
| Maximum | 127.0 | 137.8 | 129.1 | 125.6 |
| Minimum | 12.3 | 12.5 | 9.2 | 9.7 |
| SD | 34.3 | 37.1 | 35.4 | 34.3 |
| | | NK Activity (12.5:1) | | |
| average | 44.0 | 67.5 | 49.9 | 41.0 |
| Maximum | 62.0 | 97.0 | 62.0 | 56.0 |
| Minimum | 24.0 | 47.0 | 25.0 | 14.0 |
| SD | 12.2 | 16.9 | 11.4 | 14.1 |
| | | NK Activity (25:1) | | |
| average | 56.4 | 80.5 | 54.6 | 48.1 |
| Maximum | 66.0 | 100.0 | 69.0 | 63.0 |
| Minimum | 42.0 | 51.0 | 37.0 | 23.0 |
| SD | 9.8 | 13.3 | 9.5 | 12.0 |
| | | NK Activity (50:1) | | |
| average | 60.8 | 87.8 | 59.1 | 51.8 |
| Maximum | 74.0 | 100.0 | 65.0 | 63.0 |
| Minimum | 48.0 | 69.0 | 42.0 | 30.0 |
| SD | 7.5 | 10.5 | 6.9 | 11.1 |
| | | CD4 TO CD8 CELL RATIO | | |
| average | 1.45 | 1.75 | 1.64 | 1.27 |
| Maximum | 2.71 | 4.10 | 4.32 | 2.76 |
| Minimum | 0.96 | 1.05 | 0.97 | 0.58 |
| SD | 0.57 | 0.87 | 0.95 | 0.60 |

In the above subjects, fecal examination showed a mean increase of lactobacillus species from $<1\times10^{6}$ colony forming units (CFU) per gram of fecal material to $64\times10^{6}$ CFU and of bifidobacteria species from $<1\times10^{6}$ CFU to $68\times10^{6}$.

Preparations of the Strains

Strains used in the following formulation, given by way of example only, are as follows:

thermophile Streptococci (ATCC 19987) consists of a mixture of two strains from a yogurt culture and a starter used for preparation of cheeses;

Lactobacillus delbrueckii sub-species bulgaricus (ATCC 7994) is represented by a strain isolated from a yogurt culture;

Lactobacillus acidophilus (ATCC 43121) is present in a mixture consisting of two strains of human origin isolated from a special yogurt;

Bifidobacteria (Bifidobacterium infantis (ATCC 15697). Bifidobacterium longum (ATCC 15707), Bifidobacterium bifidum (ATCC 35914)) come from the intestinal flora of newborn babies;

Lactobacillus casei (ATCC 334) has been isolated from a culture employed in the production of cheeses, and Lactobacillus plantarum (ATCC 8289) has been isolated from vegetables in progress of fermentation.

In order to obviate problems due to possible phage attacks, these strains can obviously be replaced by other cultures having the same features and origins, but provided with a different phage sensitiveness.

Culture Preparation

The individual strains maintained in a lyophilized and frozen form have been grown in synthetic media specific for each species. The fundamental component of the culture medium is permeate obtained by ultrafiltration of serum or milk, to which minimal amounts of biological activators are added depending on the species. After sterilization, the culture medium is inoculated with a strain per species or 1 to 3 strains belonging to the same genotype. Cultures have been incubated upon determination of optimal parameters for each strain: temperature, time, pH values and stirring.

Industrial cultures have been concentrated by centrifugation and lyophilization has been then carried out according to standard methodologies.

After lyophilization the cell mass has been pulverized under sterile conditions. The individual cultures submitted to chemical and microbiological tests have been maintained at 5° C. in hermetic vessels.

Preparation of the Individual Species

1) Streptococcus thermophilus (ATCC 19987)

Mother

The mother has been prepared by inoculating the strain in a medium consisting of 5% of permeate +1% of yeast extract and incubated at 44° C. over 3 hours.

| | |
|---|---|
| Medium | |
| Permeate | 5% |
| Yeast extract | 1% |
| Fermentation parameters | |
| Fermenter: | 72% 1 Applikon |
| Percent of inoculation: | 1% |

-continued

| | |
|---|---|
| Incubation temperature | 44° C. |
| Stirring speed | 160 rpm |
| Neutralization set point | pH = 6.00 |
| Neutralizing substance type: | ammonium hydrate (sol to 10%) |
| Fermentation time: | 3 h 30 m |
| Final cooling: | 24° C. |
| Concentration parameters | |
| Centrifuge type: | Westfalia SA1 |
| Centrifugation temperature: | 24° C. |
| flow rate: | 24 l/h |
| (The concentrate was then centrifuged again using a laboratory centrifuge at 6000 rpm over 20 minutes). | |
| Lyophilization | |
| Lyophilizer | Edwards MINI - FAST 3400 |
| Lyophilization protector: | a solution of lactose |

Results: the number of microorganisms during the different steps of the process are reproduced in the following Table:

| Steps | U.F.C./g |
|---|---|
| End of fermentation | 2.4E9 |
| Concentrate | 1.6E11 |
| Lyophilized | 7.4E11 |

U.F.C. = Colony-forming units
E9 = one thousand millions
E11 = one hundred thousand millions No particular problems have been found in the preparation of this microorganisms. Therefore the cell loss during the different steps of the process could be greatly limited and a high bacterial charge could be achieved in the lyophilized product.

2) Lactobacillus plantarum (ATCC 8289)

Mother

Prepared in MRS culture medium and incubated at 33° C. over 5 hours.

| | |
|---|---|
| Medium | |
| Permeate | 5% |
| Yeast extract | 1% |
| Glucose | 2.5% |
| Fermentation parameters | |
| Fermenter: | Applikon |
| Percent of inoculation: | 1% |
| Incubation temperature | 33° C. |
| Stirring speed | 110 rpm |
| Neutralization set point | pH = 6.00 |
| Neutralizing substance type: | ammonium hydrate (sol to 10%) |
| Fermentation time: | 15 h |

Cell inactivation after fermentation by pasteurization at 80° C. over 15 minutes.

| | |
|---|---|
| Concentration parameters | |
| Centrifuge type: | Westfalia SA1 |
| Centrifugation temperature: | 60° C. |

-continued

| | |
|---|---|
| Flow rate: | 40 l/h |
| Lyophilization | |
| Lyophilizer | Edwards MINI - FAST 3400 |
| Lyophilization protector: | a solution of lactose |

The number of microorganisms during the different process steps is reproduced in the following Table:

| Steps | U.F.C.G | Count/g in |
|---|---|---|
| Thoma | | |
| End of fermentation | 9.2E8 | — |
| Lyophilized | — | 1.0E11 |

U.F.C. = colony-forming units
E8 = one hundred millions
E11 = one hundred thousand millions.

3) Lactobacillus casei (ATCC 334)

Mother

Prepared in MRS culture medium and incubated at 37° C. over 8 hours and 30 minutes

| | |
|---|---|
| Medium | |
| Permeate | 5% |
| Yeast extract | 1% |
| Glucose | 1% |
| Fermentation parameters | |
| Fermenter: | Applikon |
| Inoculation percent: | 1% |
| Incubation temperature | 37° C. |
| Stirring speed | 110 rpm |
| Neutralization set point | pH = 5.40 |
| Neutralizing substance type: | ammonium hydrate (sol to 10%) |
| Fermentation time: | 15 h |
| Concentration parameters | |
| Centrifuge type: | Westfalia SA1 |
| Centrifugation temperature: | 60° C. |
| Flow rate: | 46 l/h |
| Lyophilization | |
| Lyophilizer | Edwards MINI - FAST 3400 |
| Lyophilization protector: | a lactose solution |

Results: the number of microorganisms during the different process steps is reproduced in the following Table:

| Steps | U.F.C.G | Count/g in |
|---|---|---|
| Thoma | | |
| End of fermentation | 1.0E9 | — |
| Lyophilized | — | 1.0E11 |

U.F.C. = Colony-forming units
E8 = one hundred millions
E11 = one hundred thousand millions.

4) Mixture of bifidobacteria (Bifodobacterium infantis (ATCC 15697)—Bifidobacterium longum (ATCC 15707)—Bifodobacterium bifidum (ATCC 35914), ratio 1:1:1 by weight)

Mother

The mother has been prepared by inoculating the strains in a medium consisting of 10% of powdered skimmed milk +0.5% of glucose +1% of yeast extract and incubated at 38° C. over 15 hours.

| Medium | |
|---|---|
| Permeate | 4% |
| Yeast extract | 1% |
| Bacto Soytone | 0.25% |
| Glucose | 0.5% |
| **Fermentation parameters** | |
| Fermenter: | Applikon |
| Inoculation percent: | 2% |
| Incubation temperature | 38° C. |
| Stirring speed | 110 rpm |
| Neutralization set point | pH = 6.00 |
| Neutralizing substance type: | ammonium hydrate (sol to 10%) |
| Fermentation time: | 15 h |
| Cooling at the end of fermentation: | 24° C. |
| **Concentration parameters** | |
| Centrifuge type: | Westfalia SA1 |
| Centrifugation temperature: | 24° C. |
| Flow rate: | 42 l/h |
| (The obtained concentrate has been then centrifuged again with a laboratory centrifuge at 6000 rpm over 20 minutes) | |
| **Lyophilization** | |
| Lyophilizer | Edwards MINI - FAST 3400 |

Lyophilization protector: a solution of powdered skimmed milk+yeast extract+lactose+sodium maleate has been prepared.

Results: the number of microorganisms during the different process steps is reproduced in the following Table:

| Steps | U.F.C.G |
|---|---|
| End of fermentation | 1.7E9 |
| Concentrate | 7.0E10 |
| Lyophilized | 3.8E11 |

U.F.C. = Colony-forming units
E9 = one thousand millions
E10 = ten thousand millions
E11 = one hundred thousand millions.

In this case too, in which bacteria are considered of "hard" growing, no particular problems have been found during the different preparation steps and the number of microorganisms is high both in the fermentation and on the lyophilized.

5) Lactobacillus acidophilus (ATCC 43121)

Mother

Prepared in a medium consisting of 5% of permeate+1% of yeast extract+1% of glucose+1% of Tween (Registered Trademark) 80 and incubated at 37° C. over 15 hours.

| Medium | |
|---|---|
| Permeate | 5% |
| Yeast extract | 1% |
| Glucose | 1% |
| Tween (Registered Trademark) 80 | 0.1% |

-continued

| Fermentation parameters | |
|---|---|
| Fermenter: | Applikon |
| Inoculation percent: | 1% |
| Incubation temperature | 37° C. |
| Stirring speed | 110 rpm |
| Neutralization set point | pH = 6.00 |
| Neutralizing substance type: | ammonium hydrate (sol to 10%) |
| Fermentation time: | 15 h |
| Cooling at the end of fermentation: | 24° C. |
| **Concentration parameters** | |
| Centrifuge type: | Westfalia SA1 |
| Centrifugation temperature: | 24° C. |
| Flow rate: | 42 l/h |
| (The obtained concentrate has been then centrifuged again with a laboratory centrifuge at 6000 rpm over 20 minutes) | |
| **Lyophilization** | |
| Lyophilizer | Edwards MINI - FAST 3400 |

Lyophilization protector: a solution of lactose and anhydrous mixture consisting of powdered skimmed milk+yeast extract+lactose+sodium maleate+Tween (Registered Trademark) 80. Results: the number of microorganisms during the different process steps is reproduced in the following Table:

| Steps | U.F.C./g |
|---|---|
| End of fermentation | 2.9E8 |
| Concentrate | 2.3E10 |
| Lyophilized | 2.0E10 |

U.F.C. = Colony-forming units
E8 = one hundred millions
E10 = ten thousand millions 6) Lactobacillus delbrueckii sub-species bulgaricus (ATCC 7994)

Mother

Prepared in a medium consisting of 5% of permeate+1% of yeast extract+1% of beef extract+1% of glucose+0.1% of Tween (Registered Trademark) 80 and incubated at 44° C. over 4 hours and 30 minutes.

| Medium | |
|---|---|
| Permeate | 5% |
| Yeast extract | 1% |
| Beef extract | 1% |
| Glucose | 1% |
| Tween (Registered Trademark) 80 | 0.1% |
| **Fermentation parameters** | |
| Fermenter: | Applikon |
| Inoculation percent: | 1% |
| Incubation temperature | 44° C. |
| Stirring speed | 110 rpm |
| Neutralization set point | pH = 5.60 |
| Neutralization substance type: | ammonium hydrate (sol to 10%) |
| Fermentation time: | 7 h |
| Cooling at the end of fermentation: | 24° C. |
| **Concentration parameters** | |
| Installation: pilot unit for Hydro Air Research microfiltration with two serial ceramic diaphragms each | |

-continued

| | |
|---|---|
| having a 0.2 $m^2$ filtrating surface. | |
| Microfiltration temperature | 30° C. |
| Operating conditions | recirculation<br>flow rate 4000 l/h<br>input pressure<br>2.7 bar<br>output pressure<br>1.2 bar<br>average flow of<br>the permeate 30 l/h × $m^2$ |
| (The obtained concentration has been then centrifuged again with a laboratory centrifuge at 6000 rpm over 20 minutes). | |
| Lyophilization | |
| Lyophilizer | Edwards MINI - FAST 3400 |

Lyophilization protector: a solution of lactose and anhydrous mixture consisting of powdered skimmed milk+yeast extract+lactose+sodium glutamate+Tween (Registered Trademark) 80. Results: the number of micoorganisms during the different process steps is reproduced in the following Table:

| Steps | U.F.C./g |
|---|---|
| End of fermentation | 2.9E9 |
| Concentrate | 2.4E10 |
| Lyophilized | 3.5E9 |

U.F.C. = Colony-forming units
E9 = one thousand millions
E10 = ten thousand millions

What is claimed as new and desired to be secured by Letters Patent of the United States is:

1. A pharmaceutical composition comprising:

a) from 10% to 95% by weight of total composition of lyophilized Streptococcus thermophilus, and b) from 5% to 90% by weight of total composition of at least one lyophilized bacterium selected from the group consisting of Lactobacillus plantarum and Lactobacillus casei, and c) from 0% to 10% by weight of total composition a pharmaceutically acceptable excipient, wherein said Streptococcus thermophilus and the bacterium b) are present in a concentration of $1\times10^{11}$–$1\times10^{13}$ total bacteria per gram of the composition.

2. The pharmaceutical composition of claim 1 which further contains an excipient in an amount of 1 to 10% by weight based on total composition.

3. The pharmaceutical composition of claim 2, wherein said excipient is selected from the group consisting of maltodextrin, microcrystalline cellulose, maize starch, levulose, lactose and dextrose.

4. The pharmaceutical composition of claim 1 which further contains from 85% to 5% by weight of one or more lyophilized bacteria selected from the group consisting of bifidobacteria, Lactobacillus acidophilus, Lactobacillus delbrueckii sub-species bulgaricus and Streptococcus faecium, wherein the concentration of this bacterium is from $1\times10^{9}$ to $1\times10^{12}$ bacteria per gram of the composition.

5. The pharmaceutical composition of claim 4, wherein said bifidobacteria is a mixture of Bifidobacterium longum, Bifidobacterium bifidum and Bifidobacterium infantis is approximately in equal weight distribution.

6. The pharmaceutical composition of claim 1, which further comprises from 1 to 20% by weight of total composition of a drug which is compatible with the bacteria in said composition.

7. The pharmaceutical composition of claim 6, wherein said drug is selected from the group consisting of anticholinergics, antihistamines, analgesics, adrenergics, antiinflammatories, antiseptics, hepatoprotective agents and antilipemics.

8. The pharmaceutical composition according to claim 1, which contains 1 to 10% by weight of total composition of said pharmaceutically acceptable excipient.

9. A pharmaceutical composition comprising:

(a) from 30–35% by weight of lyophilized Streptococcus thermophilus;

(b) from 7–10% by weight of lyophilized Lactobacillus casei;

(c) from 8–10% by weight of lyophilized Lactobacillus plantarum;

(d) from 7–10% by weight of lyophilized Lactobacillus acidophilus;

(e) from 8–10% by weight of lyophilized Lactobacillus delbrueckii sub-species bulgaricus;

(f) from 27–30% by weight of a mixture of lyophilized bifidobacteria; and (g) from 8–10% by weight of a pharmaceutically acceptable excipient, wherein all amounts are based on the total weight of the composition and said bifidobacteria is a mixture of Bifidobacterium longum, Bifidobacterium infantis, and Bifidobacterium bifidum;

wherein said excipient is selected from the group consisting of maltodextrin, levulose, microcrystalline cellulose, maize starch, lactose, and dextrose; and wherein said Streptococcus thermophilus, said Lactobacillus casei, and said Lactobacillus plantarum are present in said pharmaceutical composition in a total concentration of $1\times10^{11}$ to $1\times10^{13}$ bacteria per gram.

10. The pharmaceutical composition of claim 9, wherein said bifidiobacteria is a mixture 1:1:1 by weight.

11. A method for treating hypercholesteremia, comprising administering to a patient in need thereof an effective amount of a composition, said composition comprising:

(a) from 10 to 95% by weight of total composition of lyophilized Streptococcus thermophilus;

(b) from 5 to 90% by weight of total composition of at least one lyophilized bacteria selected from the group consisting of Lactobacillus plantarum and Lactobacillus casei; and (c) from 0 to 10% by weight of total composition of a pharmaceutically acceptable excipient;

wherein said Streptococcus thermophilus, Lactobacillus plantarum, and Lactobacillus casei are present in such amounts that the total bacteria concentration in said composition is $1\times10^{11}$ to $1\times10^{13}$ total bacteria per gram of composition.

12. The method of claim 11, wherein said composition comprises 1 to 10% by weight of said excipient.

13. The method of claim 12, wherein said excipient is selected from the group consisting of maltodextrin, microcrystalline cellulose, maize starch, levulose, lactose, and dextrose.

14. The method of claim 11, wherein said composition further comprises from 85% to 5% by weight of one or more lyophilized bacteria selected from the group consisting of bifidobacteria, Lactobacillus acidophilus, Lactobacillus delbrueckii sub-species bulgaricus and Streptococcus faecium, in a concentration of from $1\times10^9$ to $1\times10^{12}$ bacteria per gram of said composition.

15. The method of claim 14, wherein said bifidobacteria is a mixture of Bifidobacterium longum, Bifidobacterium bifidum and Bifidobacterium infantis in approximately an equal weight distribution.

16. The method of claim 11, wherein said composition comprises:

(a) from 30–35% by weight of lyophilized Streptococcus thermophilus;

(b) from 7–10% by weight of lyophilized Lactobacillus casei;

(c) from 8–10% by weight of lyophilized Lactobacillus plantarum;

(d) from 7–10% by weight of lyophilized Lactobacillus acidophilus;

(e) from 8–10% by weight of lyophilized Lactobacillus delbrueckii sub-species bulgaricus;

(f) from 27–30% by weight of lyophilized bifidobacteria; and (g) from 8–10% by weight of an excipient, wherein all amounts are based on the total weight of said composition and said bifidobacteria is a mixture 1:1:1 by weight of Bifidobacterium longum, Bifidobacterium infantis, and Bifidobacterium bifidum, and said excipient is selected from the group consisting of maltodextrin, levulose, microcrystalline cellulose, maize starch, lactose, and dextrose.

17. The method of claim 11, wherein said administering is oral administration.

18. A method for treating a gastrointestinal disorder, comprising administering to a patient in need thereof an effective amount of a composition, said composition comprising:

(a) from 10 to 95% by weight of total composition of lyophilized Streptococcus thermophilus;

(b) from 5 to 90% by weight of total composition of at least one lyophilized bacteria selected from the group consisting of Lactobacillus plantarum and Lactobacillus casei; and (c) from 0 to 10% by weight of total composition of a pharmaceutically acceptable excipient;

wherein aid Streptococcus thermophilus, Lactobacillus plantarum, and Lactobacillus casei are present in such amounts that the total bacteria concentration in said composition is $1\times10^{11}$ to $1\times10^{13}$ total bacteria per gram of composition.

19. The method of claim 18, wherein said composition comprises 1 to 10% by weight of said excipient.

20. The method of claim 19, wherein said excipient is selected from the group consisting of maltodextrin, microcrystalline cellulose, maize starch, levulose, lactose, and dextrose.

21. The method of claim 18, wherein said composition further comprises from 85% to 5% by weight of one or more lyophilized bacteria selected from the group consisting of bifidobacteria, Lactobacillus acidophilus, Lactobacillus delbrueckii sub-species bulgaricus, and Streptococcus faecium, in a concentration of from $1\times10^9$ to $1\times10^{12}$ bacteria per gram of said composition.

22. The method of claim 21, wherein said bifidobacteria is a mixture of Bifidobacterium longum, Bifidobacterium bifidum, and Bifidobacterium infantis in approximately an equal weight distribution.

23. The method of claim 18, wherein said composition comprises:

(a) from 30–35% by weight of lyophilized Streptococcus thermophilus;

(b) from 7–10% by weight of lyophilized Lactobacillus casei;

(c) from 8–10% by weight of lyophilized Lactobacillus plantarum;

(d) from 7–10% by weight of lyophilized Lactobacillus acidophilus;

(e) from 8–10% by weight of lyophilized Lactobacillus delbrueckii sub-species bulgaricus;

(f) from 27–30% by weight of lyophilized bifidobacteria; and (g) from 8–10% by weight of an excipient, wherein all amounts are based on the total weight of said composition and said bifidobacteria is a mixture 1:1:1 by weight of Bifidobacterium longum, Bifidobacterium infantis and Bifidobacterium bifidum, and said excipient is selected from the group consisting of maltodextrin, levulose, microcrystalline cellulose, maize starch, lactose, and dextrose.

24. The method of claim 18, wherein said administering is oral administration.

25. The method of claim 18, wherein said gastrointestinal disorder is diarrhea.

26. The method of claim 18, wherein said gastrointestinal disorder is irritable bowel syndrome.

27. A method for modulating a host's immune response, comprising administering to a patient in need thereof an effective amount of a composition, said composition comprising:

(a) from 10 to 95% by weight of total composition of lyophilized Streptococcus thermophilus;

(b) from 5 to 90% by weight of total composition of at least one lyophilized bacteria selected from the group consisting of Lactobacillus plantarum and Lactobacillus casei; and (c) from 0 to 10% by weight of total composition of a pharmaceutically acceptable excipient;

wherein said Streptococcus thermophilus, Lactobacillus plantarum, and Lactobacillus casei are present in such amounts that the total bacteria concentration in said composition is $1\times10^{11}$ to $1\times10^{13}$ total bacteria per gram of composition.

28. The method of claim 27, wherein said composition comprises 1 to 10% by weight of said excipient.

29. The method of claim 28, wherein said excipient is selected from the group consisting of maltodextrin, microcrystalline cellulose, maize starch, levulose, lactose, and dextrose.

30. The method of claim 27, wherein said composition further comprises from 85% to 5% by weight of one or more lyophilized bacteria selected from the group consisting of bifidobacteria, Lactobacillus acidophilus, Lactobacillus delbrueckii sub-species bulgaricus, and Streptococcus faecium, in a concentration of from $1\times10^9$ to $1\times10^{12}$ bacteria per gram of said composition.

31. The method of claim 30, wherein said bifidobacteria is a mixture of Bifidobacterium longum, Bifidobacterium bifidum and Bifidobacterium infantis in approximately an equal weight distribution.

32. The method of claim 27, wherein said composition comprises:

(a) from 30–35% by weight of lyophilized Streptococcus thermophilus;

(b) from 7–10% by weight of lyophilized Lactobacillus casei;

(c) from 8–10% by weight of lyophilized Lactobacillus plantarum;

(d) from 7–10% by weight of lyophilized Lactobacillus acidophilus;

(e) from 8–10% by weight of lyophilized Lactobacillus delbrueckii sub-species bulgaricus;

(f) from 27–30% by weight of lyophilized bifidobacteria; and (g) from 8–10% by weight of an excipient, wherein all amounts are based on the total weight of said composition and said bifidobacteria is a mixture 1:1:1 by weight of Bifidobacterium longum, Bifidobacterium infantis, and Bifidobacterium bifidum, and said excipient is selected from the group consisting of maltodextrin, levulose, microcrystalline cellulose, maize starch, lactose, and dextrose.

33. The method of claim 27, wherein said administering is oral administration.

* * * * *